United States Patent [19]

Friese

[11] Patent Number: 4,490,894
[45] Date of Patent: Jan. 1, 1985

[54] APPARATUS FOR ATTACHING A WITHDRAWAL CORD TO A TAMPON

[75] Inventor: Axel Friese, Wuppertal, Fed. Rep. of Germany

[73] Assignee: Dr. Carl Hahn, G.m.b.H., Dusseldorf, Fed. Rep. of Germany

[21] Appl. No.: 414,093

[22] Filed: Sep. 1, 1982

[30] Foreign Application Priority Data

Sep. 3, 1981 [DE] Fed. Rep. of Germany ....... 3134957

[51] Int. Cl.³ ............................................. A61F 13/20
[52] U.S. Cl. .................................................. 28/120
[58] Field of Search .......................... 28/118, 119, 120

[56] References Cited

U.S. PATENT DOCUMENTS

| | | | |
|---|---|---|---|
| 2,584,913 | 2/1952 | Parish | 28/120 X |
| 2,624,078 | 1/1953 | Winter et al. | 28/120 X |
| 4,012,809 | 3/1977 | Warncke et al. | 28/120 |

FOREIGN PATENT DOCUMENTS 2355962  2/1975  Fed. Rep. of Germany .

Primary Examiner—Robert R. Mackey
Attorney, Agent, or Firm—Jason Lipow

[57] ABSTRACT

An apparatus is provided for attaching a withdrawal tape to a catamenial tampon. The apparatus is designed so that the withdrawal cord is frictionally wound up upon a centering mandrel in a controlled manner and then pressed against the withdrawal end of a tampon to provide a spiral of withdrawal cord in the same uniform shape and quality while manufacturing such tampons at high speed. The withdrawal cord is picked up by a driver and wound up in an annular chamber between a centering mandrel and the driver. The driver comprises two cylindrical driver shelves arranged concentrically to one another at a radial distance and each having a driver tooth. The cooperation between the driver teeth and the two driver shelves makes it possible to perfectly guide the withdrawal cord during the course of winding the same.

13 Claims, 7 Drawing Figures

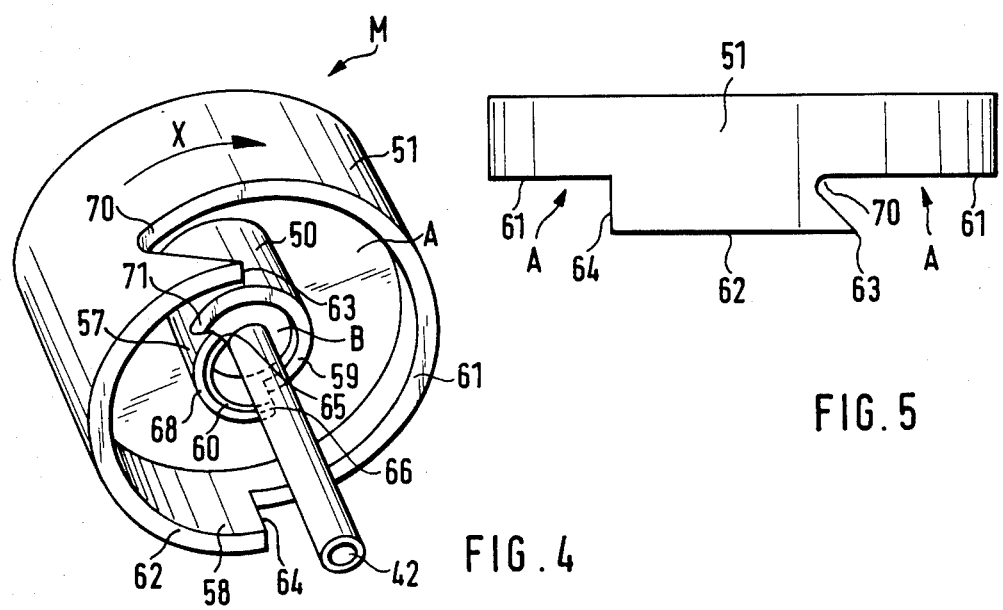
FIG. 4
FIG. 5
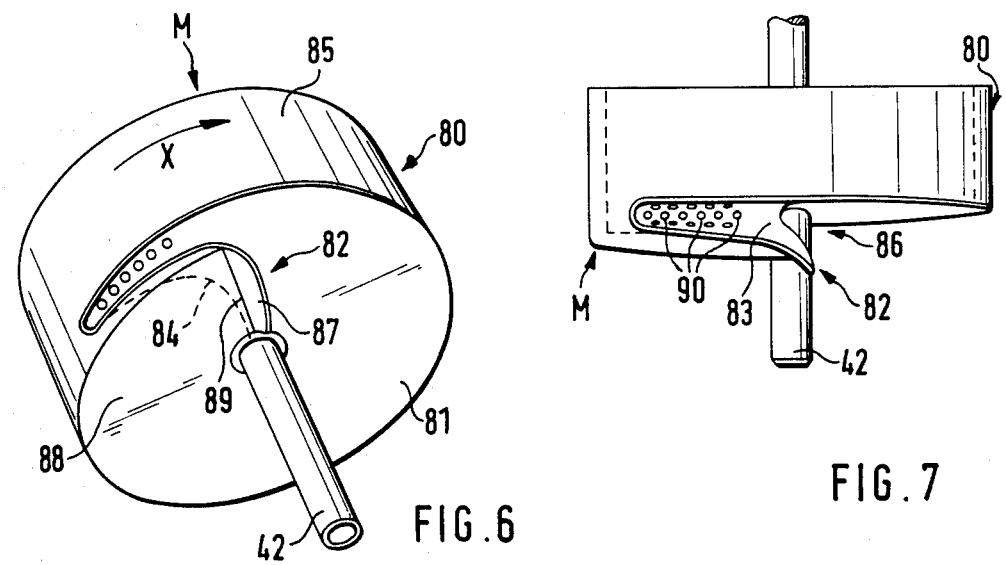
FIG. 6
FIG. 7

APPARATUS FOR ATTACHING A WITHDRAWAL CORD TO A TAMPON

BACKGROUND OF THE INVENTION

The invention relates to a device for attaching a withdrawal cord in the form of a regular wound spiral to the withdrawal end of a tampon and, in particular, a tampon for female hygiene.

A device of this generic type is known from German Auslegeschrift No. 2,355,962. This device consists of a flow chamber into which a tampon with a withdrawal cord loosely hanging down is inserted and which can be closed on the insertion side. A blow mandrel with an air outlet orifice at its front end can be introduced into the flow channel. The blow mandrel is coaxially surrounded by a press ram which is displaceable to and fro in the direction of its longitudinal axis, independently of the blow mandrel. The blow mandrel is moved forward in the direction of the tampon for such a distance that its air outlet orifice almost touches the tampon. The blow air is then switched on and flows against the end of the tampon, is deflected there and is removed either through a ring channel located between the press ram and the inner wall of the flow chamber or through air-discharge channels between the press ram and the guide channel. The deflection of the air causes turbulent flow which grips the withdrawal cord and takes it along. The blow mandrel is retracted and the withdrawal cord is gripped by the press ram which winds up the withdrawal cord, approximately in the form of a spiral, and presses it against the rear end of the tampon. The end face of the press ram is roughened. This known device has the disadvantages that the power consumption for the necessary compressed air is considerable and that the mode of operation is unreliable because it cannot be guaranteed that the withdrawal cord will be wound up regularly onto the blow mandrel, and subsequently pushed off against the withdrawal end of the tampon, with the reliability and speed and control desirable for a massproduced article.

SUMMARY OF THE INVENTION

It is therefore the object of the invention to improve the device mentioned at the outset in such a way that the withdrawal cord is frictionally wound up onto the centering mandrel in a controlled manner and can then be pressed against the withdrawal end of the tampon in an always uniform shape and quality.

The advantage achieved by the invention is that the withdrawal cord can be reliably taken along by the driver and can be wound up, in an annular chamber between the centering mandrel and the driver, in a regular manner onto the centering mandrel to give a wound spiral and can be pressed, in a perfect and always constant shape, by the push-off ram from the centering mandrel against the withdrawal end of the tampon, where it is self-holding, so that the processing quality is constant for every tampon, in spite of mass production. The regular wound spiral enables the user to accustom herself to handling the tampon always in the same way and, even under adverse conditions, to be able to pull the withdrawal cord slightly away from the withdrawal end of the tampon, before the latter is used, so that the later removal of the tampon from the body cavity is always ensured.

According to an embodiment of the invention, the driver consists of two cylindrical driver shells which are arranged concentrically to one another at a radial distance and each have one driver tooth. This embodiment is simple and cheap to manufacture and has a low weight due to the small requirement of materials.

In this first embodiment, it is advisable for the driver tooth of the outer driver shell to project axially, as compared with the driver tooth of the inner driver shell, in the direction of the mold, while the tooth roots of both the driver teeth are arranged in a common plane which extends perpendicular to the axis of rotation of the two driver shells. The outer, axially projecting driver tooth ensures reliable gripping of that part of the withdrawal cord which hangs down from the withdrawal end of the tampon, and the arrangement of the tooth roots on the driver teeth in a common plane makes it possible perfectly to guide the withdrawal cord by means of the two driver shells.

Improved guiding of the withdrawal cord while the driver shells rotate can be achieved when the driver tooth on the outer driver shell is offset forward, in the direction of rotation of the latter, relative to the driver tooth of the inner driver shell. This angular forward offset of the outer driver tooth relative to the inner driver tooth should be at least 10°.

While further specific embodiments relate to an advantageous constructional form of the driver shells, the fact that the cut-outs provided for forming the driver teeth in the two driver shells extend over an angle of at least 180° ensures that, over the largest possible angle of rotation of the two driver shells, the withdrawal cord can pass into the range of action of the driver teeth.

In a specific embodiment, the withdrawal cord can be wound up directly on the push-off ram so that only a short stroke motion of the latter is necessary in order to push off the regular wound spiral, formed from the withdrawal cord, against the withdrawal end of the tampon.

The conical design of the end face of the inner driver shell and the correspondingly conical design of the inner edge of the orifice of the mold make it possible perfectly to transfer the wound spiral towards the withdrawal end of the tampon in the mold, or smoothly to guide the withdrawal cord.

According to another embodiment, the driver can consist of a cylindrical driver shell, of which the front end face located opposite the mold has the shape of an axial helical face, the front or outer end of the helical face being axially undercut with the formation of a cord-guiding groove which is open in the direction of rotation.

A driver shell having the features of still another embodiment ensures an always perfect contact and guiding of the withdrawal cord in the cord-guiding groove during the rotation of the driver shell.

As is described herein, a catching lip of the cord-guiding groove ensures that the withdrawal cord is reliably gripped, while air passage orifices in the wall of the cord-guiding groove further improve the reliable contact of the withdrawal cord in the cord-guiding groove, because the withdrawal cord is pressed against the bottom of the cord-guiding groove by the air flowing through the passage orifices and the tension thus generated makes it possible, during the winding-up of the withdrawal cord, to form a regular wound spiral on the centering mandrel in an always constant quality.

BRIEF DESCRIPTION OF THE DRAWINGS

The invention is illustrated, by way of example and diagrammatically, in the drawings in which:

FIG. 4 shows a perspective view of a first embodiment of a driver, having an inner and an outer driver shell, and a centering mandrel;

FIG. 5 shows a developed view of the outer driver shell in FIG. 4;

FIG. 6 shows a perspective front view of a second embodiment of a driver; and

FIG. 7 shows a plan view of the driver in FIG. 6.

DETAILED DESCRIPTION OF THE INVENTION

Figure 1:
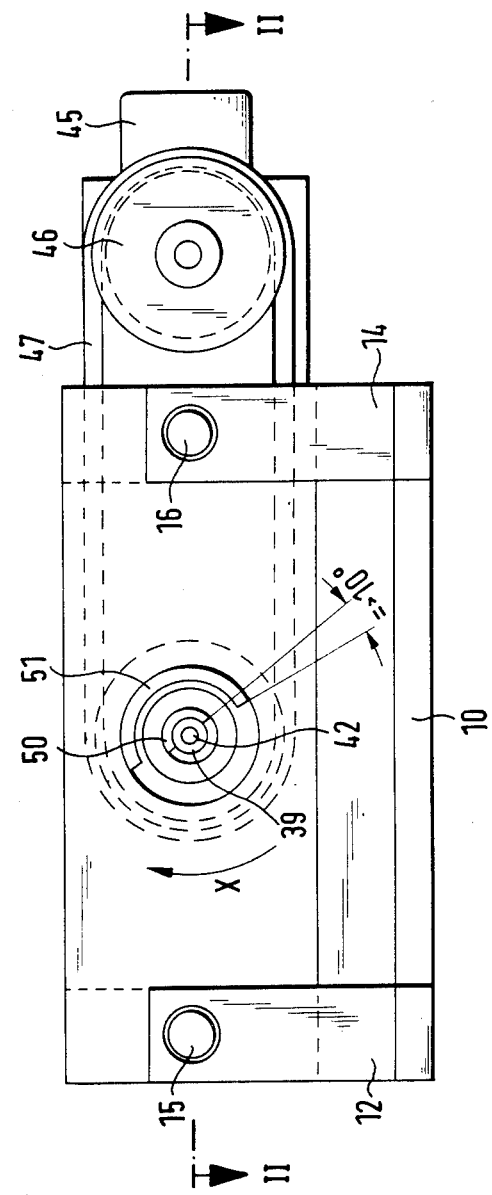
FIG. 1 shows a device for the winding-up and pressing-on of the withdrawal cord of a tampon, in a front view.
Figure 2:
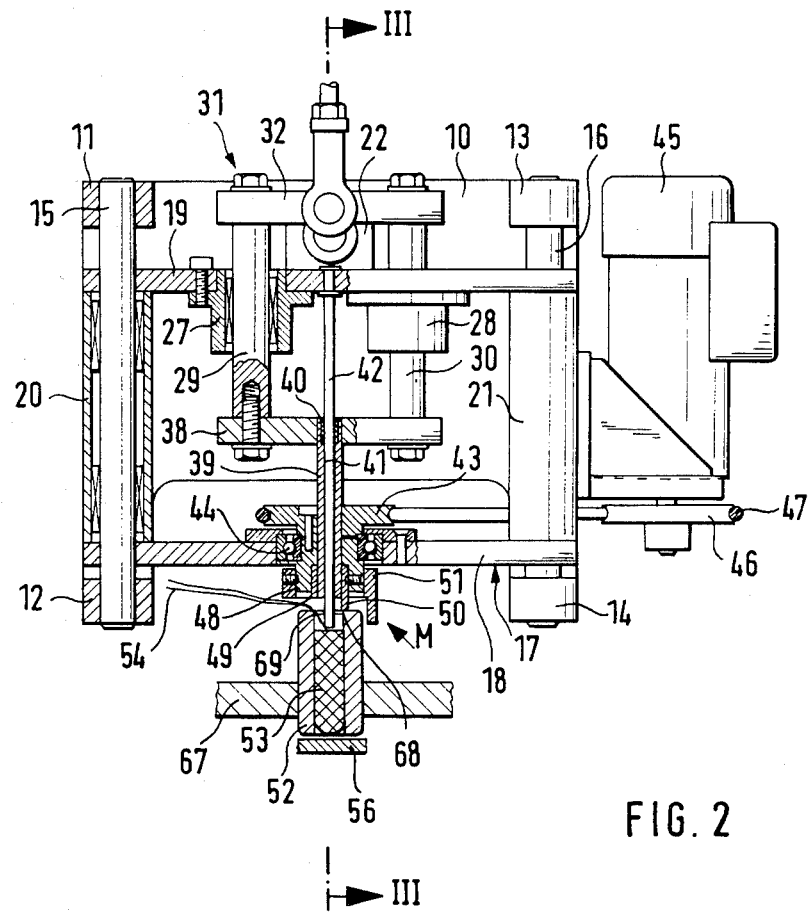
FIG. 2 shows a plan view of a horizontal section along line II—II in FIG. 1.
Figure 3:
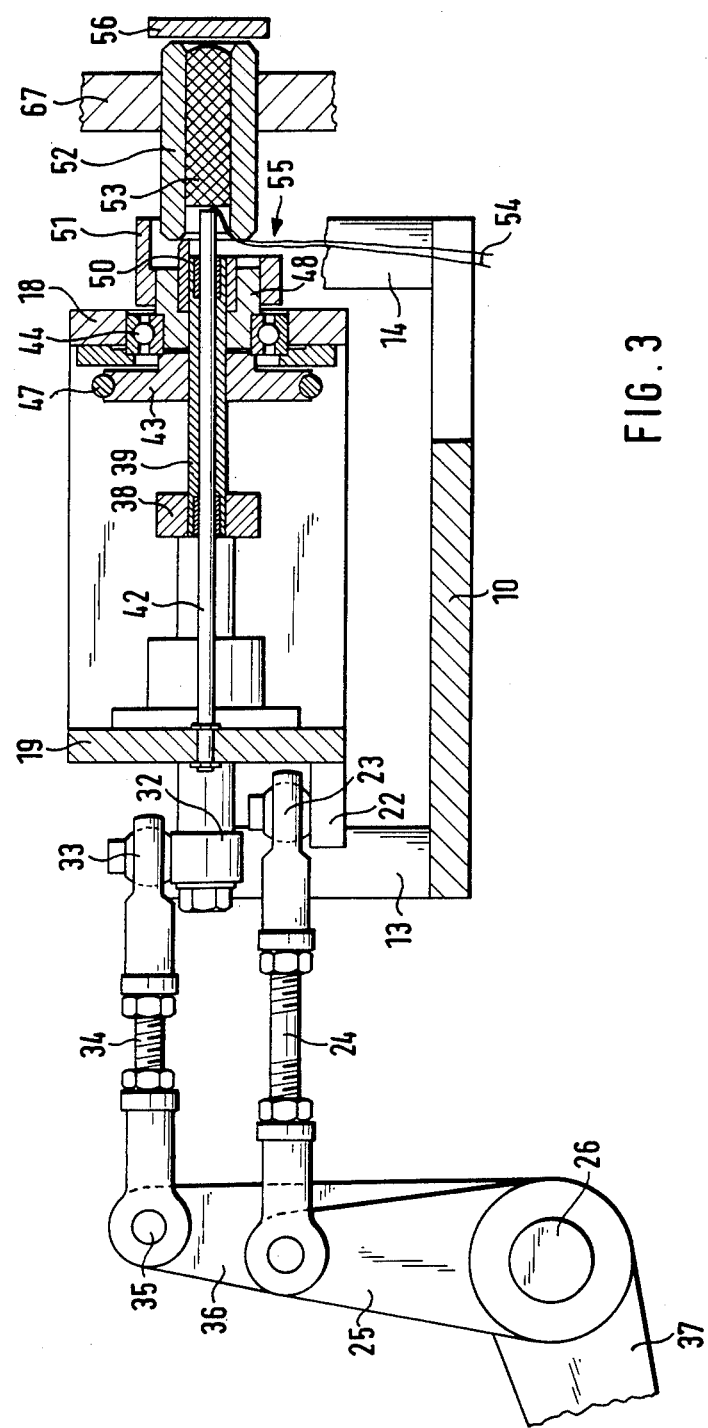
FIG. 3 shows a cross-section along line III—III in FIG. 2.

According to FIGS. 1 to 3, the device for attaching the free end of a withdrawal cord of a tampon, intended particularly for female hygiene, consists of a fixed baseplate 10, four columns 11, 12, 13, 14 projecting upwards from the corners thereof. The upper ends of the columns 11, 12, 13, 14 in pairs carry sliding rods 15 and 16 which are arranged at the same height at a distance, and parallel to one another and to the short sides of the base plate 10. A frameshaped driver carriage 17 consists of two vertical front and rear walls 18, 19 which, at a distance, are parallel to one another and to the long sides of the baseplate 10. The front wall 18 and the rear wall 19 are separated from one another by guide bushes 20, 21 which are mounted on sliding rods 15, 16 to be displaceable to and fro. For this purpose, a strip 22, from which a spherical gudgeon 23 projects upwards, is fitted to the bottom of the outside of the rear wall 19 (FIG. 3). One end of a draw bar 24 is hinged to the spherical gudgeon 23, and its other end is pivotally joined to a lever 25. The lever 25 is pivotable about a pivot axis 26, and its other end is joined, in a manner which is known and therefore not shown in detail, to a rod linkage 37 which engages (FIG. 3) a control cam, so that the driver carriage can be moved horizontally to and fro.

According to FIG. 2, two bush-type guides 27, 28 are provided in the rear wall 19 of the driver carriage 17 and these are arranged at a distance from one another at the same height as the sliding rods 15, 16, parallel to and between the latter. One push-rod 29, 30 of a push-off ram carriage 31 passes through each of these guides, and the ends, projecting outwards through the rear wall 19 of the driver carriage 17, are connected to one another by a yoke 32 and their ends projecting inwards through the rear wall are connected by a tie rod 38. The yoke 32 carries a spherical gudgeon 33 for joining a draw bar 34 (FIG. 3) which is fixed via a joint 35 to a lever 36. The lever 36 in turn is pivotable about the pivot axis 26 and its other lever arm 37 is connected to a leverage system which is not shown and which, in a manner which is known per se and therefore not illustrated engages a conrol cam in such a way that the push-off ram carriage 31 is horizontally movable to and fro.

The rear end of a sleeve-type push-off ram 39 is seated in a bore 40 of the tie rod 38 and is arranged at a distance from and parallel to the sliding rods 15, 16 in a horizontal plane. A centering mandrel 42 passes coaxially through a central bore 41 of the push-off ram 39, the rear end of the centering mandrel being fixed to the rear wall 19 of the driver carriage 17 and its front end projecting from the front opening of the push-off ram 39 and the front wall 18 of the driver carriage 17. The centering mandrel is thus taken along by the driver carriage 17 which takes up the push-off ram to be movable in parallel on the centering mandrel 42.

On the rear of the front wall 18 of the driver carriage 17, a pulley 43 is arranged coaxially to the push-off ram 39 and the centering mandrel 42 and is rotatably mounted by means of ball bearings 44 in the front wall 18. The pulley 43 can be driven by a motor 45 which is fixed to the driver carriage 17 and the pulley 46 of which is connected via an endless belt 47 to the pulley 43. The pulley 43 is releasably fitted to the rear of a bearing part 48, in the front recess 49 of which an inner driver shell 50 of a driver M is fixed. An outer driver shell 51 of the driver M is releasably and adjustably joined to the outer cylindrical surface of the bearing part 48. The driver shells 50, 51 are described in more detail below. Of course, the motor can be arranged in a fixed position and coupled to the pulley 43 via a tooth drive or belt drive which permits a longitudinal displacement of the driver carriage 17.

At any time, a mold 52 of an indexing turret 67 is located, at a distance, coaxially opposite the centering mandrel 42 and the inner and outer driver shells 50, 51. The mold 52 contains a finished pressed tampon 53, of which the withdrawal end, facing the centering mandrel 42, has a withdrawal cord 54 which extends out of the mold 52 through the axial interspace 55 formed by that mold and the driver shells 50, 51. The mold 52 can be heated so that the pressed tampon 53 can be made dimensionally stable by the action of heat. The end of the mold 52, which faces away from the centering mandrel 42, is located, at a small distance, opposite an abutment 56 for the tampon 53 present in the mold 52; this abutment can be formed by a fixed plate.

According to FIGS. 4 and 5, the inner and the outer driver shells 50, 51 have a cylindrical shape and are arranged, secure against rotation, concentrically to the axis of the bearing part 48. On the side facing the mold 52, the two driver shells 50, 51 each have a cut-out A or B which extends over a peripheral angle of about 180°, so that in each case an approximately half-cylindrical shell sector 57, 58 and approximately half-cylindrical rear and front end faces 59, 60, and 61, 62, which are axially offset from one another, are formed. The end face 61 of the cut-out A of the outer driver shell 51 is located at the height of the end face of the push off ram 39 in the rest position of the latter. The shell sector 58 protrudes axially from the transverse plane, in which the rear end faces 59 and 61 of the two driver shells are located, by about twice the axial length of the shell sector 57 of the inner driver shell. An outer driver tooth 63, therefore, also projects axially relative to an inner driver tooth 65, so that reliable gripping of the withdrawal cord 54 of the tampon 53 is ensured.

As can be seen from FIG. 1, the two driver teeth 63, 65 of the driver shells 50 and 51 form an angle of at least 10°, the outer driver tooth 63 being offset forward, in the direction of rotation x, relative to the inner driver tooth 65. Towards the end of the process of winding up the withdrawal cord 54, the inner driver shell 50 is at a small distance in front of the mold 52.

The developed view of the peripheral surface of the outer driver shell 51 in FIG. 5 shows that the cut-out A forms the undercut driver tooth 63 on the side which is in front in the direction of rotation x, forms an edge 64 parallel to the axis on the side which is at the rear in the direction of rotation x and forms the end face 61 at the front end. The cut-out A extends over an axial depth which corresponds approximately to half the axial length of the outer driver shell 51.

Analogously to FIG. 5, the cut-out B of the inner driver shell 50 forms a driver tooth 65 and also an edge 66 parallel to the axis. During winding-up, the end faces 59 and 61, and the end face of the push-off ram 39, are in one plane.

It will be seen that the front end face 60 of the inner driver shell 50 has a conical chamfer 68 on the outside. The cone angle of this chamfer 68 approximately corresponds to the cone angle of a conical chamfer 69 of the mold 52 in the zone of the inner edge of its end face, the outer edge of which is chamfered rearwards, in such a way that the inner driver shell 50 can approach the mold 52 up to a distance of 0.1 to 0.2 mm, without the outer driver shell 51 touching the mold 52.

In the working position, the driver carriage 17 with the inner and outer driver shells 50 and 51, and the push-off ram carriage 31, are in the retracted position. In this position of the mold 52, coaxial to the centering mandrel 42, to the driver shells 50, 51 and to the push-off ram 39, the withdrawal cord 54 of the tampon 53 extends through the axial interspace 55 between the inner driver shell 50 and the end face of the mold 52 as well as the outer driver shell 51. The driver carriage 17 is then moved forwards by means of the draw bar 24 in the direction of the mold 52, the driver shells 50 and 51 being continuously rotated clockwise by the motor 45 via the pulleys 43 and 46.

As a result of the rotary movement, the driver tooth 63 of the outer driver shell 51 grips the withdrawal cord 54 which freely hangs down from the withdrawal end of the tampon 53 and thus comes into contact with the tooth root 70 of the outer driver tooth 63. Since the front end of the centering mandrel 42 protrudes coaxially into the mold 52 up to the withdrawal end of the tampon 53, the withdrawal cord 54 is wound up about the centering mandrel 42. The free end of the withdrawal cord 54 is thus increasingly shortened until it finally is moved inwards and out of the path of movement of the outer driver shell 51. After this, the inner driver shell 50 with the driver tooth 65 and the tooth root 71 which, together with the tooth root 70 of the outer driver shell 51, is located in a common plane extending perpendicular to the axis of rotation of the two driver shells, comes into action and winds up the remainder of the withdrawal cord 54 to give a regular spiral.

During the winding-up step, the push-off ram carriage 31 with the push-off ram 39 is moved forwards by means of the draw bar 34 in the direction of the tampon 53, so that the withdrawal cord 54, which has been wound up as a helix or wound spiral onto the centering mandrel 42, is pressed in regular shape by the push-off ram 39 against the withdrawal end of the tampon 53, while at the same time the driver carriage 17 with the centering mandrel 42 is retracted. This transfer proceeds smoothly in view of the fact that the cylindrical internal diameter of the inner driver shell 50 exactly corresponds to that of the mold 52 and, as mentioned, the gap between the inner driver shell 50 and the mold 52 is very small.

FIGS. 6 and 7 show a second embodiment of a driver M in the form of a cylindrical driver shell 80 which is open on the side facing away from the mold 52 and has a helical face 81 on the side facing the mold. The outer end 82, facing the mold 52, of this helical face 81 is undercut, forming a cord-guiding groove 83. This cord-guiding groove 83, the groove bottom 84 of which is indicated in dashes in FIG. 6, extends on the inner half of the radius of the driver shell 80 at first predominantly radially outwards and only to a relatively small extent against the direction of rotation x in the peripheral direction, but then changes its direction in the second outer half of the radius of the driver shell 80 in such a way that, increasingly, it extends predominantly in the peripheral direction against the direction of rotation x and to a smaller extent radially outwards, until it runs out into the cylindrical peripheral surface 85 coaxial to the push-off ram 39.

The cross-section of the groove widens towards the opening 86 of the groove, the outer wall of the cord-guiding groove 83 being bent, in the zone of its outer end, as a catching lip 87 axially out of the helical face 88. In the region of the line 89, this catching lip 87 passes through the outer helical face 88. In its rear section which runs predominantly in the peripheral direction, the cord-guiding groove 83 is preferably provided with air passage orifices 90, through which air can flow, when the driver shell 80 rotates in the direction of the arrow x, and can thus securely hold the withdrawal cord 54 of the tampon 53 against the bottom 84 of the cord-guiding groove 83. In this way, the withdrawal cord 54 is continuously and securely held against the groove bottom 84, while it is wound up on the centering mandrel 42, while it is drawn in the direction of the centering mandrel 42 during the rotary movement of the driver shell 80.

As shown in FIG. 3, the driver shell 80 is rotatably mounted in the front wall 18 of the driver carriage 17 by means of the ball bearing 44 and is connected to the pulley 43 so that it can continuously be driven in the direction of rotation x by the motor 45.

I claim:

1. In a device for manufacturing a tampon of the type having a withdrawal end and a withdrawal cord wound into a spiral and pressed into the withdrawal end of the tampon wherein the tampon is held in a cylindrical mold open at the withdrawal end of the tampon, with the withdrawal string extending out of the open mold; an improved means for winding the withdrawal cord into said spiral and for pressing said spiral into the withdrawal end of the tampon comprising:
   a driver carriage facing the open end of the mold;
   an axially extending centering mandrel affixed to the carriage and movable coaxially with respect to the mold;
   an axially extending push off ram surrounding said centering mandrel and axially movable with respect to the cylindrical mold;
   a driver surrounding and rotatably mounted about said push off ram, said driver having withdrawal cord gripping means;
   means for moving said centering mandrel into close proximity with the end of said tampon;
   means for rotating said driver about said push off ram whereby said gripping means grips said extending withdrawal cord and winds said cord about said centering mandrel; and means for axially moving said push off ram against said wound cord to push said cord off of said centering mandrel and press the wound cord against the withdrawal end of the tampon.

2. A device as claimed in claim 1, wherein the driver consists of two cylindrical driver shells which are arranged concentrically to one another at a radial distance and each have one driver tooth.

3. A device as claimed in claim 2, wherein the driver tooth of the outer driver shell projects axially, as compared with the driver tooth of the inner driver shell, in the direction of the mold, but the tooth roots of both the driver teeth lie in a common plane which extends perpendicular to the axis of rotation of the two driver shells.

4. A device as claimed in claim 2, wherein the driver tooth of the outer driver shell is offset forward, in the direction of rotation, relative to the driver tooth of the inner driver shell.

5. A device as claimed in claim 4, wherein the angular forward offset of the outer driver tooth relative to the inner driver tooth is at least 10°.

6. A device as claimed in claim 2, wherein the driver teeth of the two cylindrical driver shells are formed by a cut-out on the end face thereof, and the tooth root of the outer driver tooth and the inner driver tooth each run out into the front end face, having the form of a circular arc, of the cut-outs of the two driver shells.

7. A device as claimed in claim 6, wherein the cut-outs of the two driver shells extend over an angle of at least 180°.

8. A device as claimed in claim 6, wherein the axial depth of the cut-out of the outer driver shell extends up to the plane of the annular circular end face of the push-off ram in the retracted rest position of the latter.

9. A device as claimed in claim 6, wherein the circular annular end face of the inner driver shell is a chamfer conically tapering towards its outer end and is located opposite a correspondingly shaped end face of the mold, and the inner driver shell can be brought into very close approach to said end face of the mold.

10. A device as claimed in claim 1, wherein the driver consists of a cylindrical driver shell, of which the front end face located opposite the mold has the shape of an axial helical face, the front or outer end of the helical face being axially undercut with the formation of a cord-guiding groove which is open in the direction of rotation of the driver shell.

11. A device as claimed in claim 10, wherein the cord-guiding groove is trough-shaped and extends from the hub of the driver shell at first essentially radially, only by a very small amount against its direction of rotation, and then extends predominantly against the direction of rotation thereof only in the region of the outer half of the radius of the driver shell, but then extends radially outwards only by a small amount up to the cylindrical peripheral surface of the driver shell.

12. A device as claimed in claim 11, wherein the outer wall of the trough-shaped cord-guiding groove is bent out of the helical face on the end face of the driver shell in the axial direction, the cross-section of the groove being widened, in the zone of its outer edge, as a catching lip for the withdrawal cord.

13. A device as claimed in claim 10, wherein at least that zone of the cord-guiding groove which is located in the outer half of the radius of the driver shell is provided with air passage orifices going through the wall of the cord-guiding groove.

* * * * *